US005861525A

United States Patent [19]
Lennon et al.

[11] Patent Number: 5,861,525
[45] Date of Patent: Jan. 19, 1999

[54] METHOD FOR PREPARING CYANOPHOSPHONATE DERIVATIVES FROM PHOSPHATE ESTERS AND CYANIDE

[75] Inventors: Patrick J. Lennon, Webster Grove; Sergey G. Vulfson, Chesterfield, both of Mo.

[73] Assignee: Monsanto Company, St. Louis, Mo.

[21] Appl. No.: 996,947

[22] Filed: Dec. 23, 1997

Related U.S. Application Data

[60] Provisional application No. 60/034,523, Dec. 30, 1996.
[51] Int. Cl.[6] .................. C07F 9/40; C07F 9/38
[52] U.S. Cl. .................. 558/87; 423/302; 558/145; 558/166; 558/167; 562/16
[58] Field of Search ............... 423/302; 558/87, 558/145, 166, 167; 562/16

[56] References Cited

U.S. PATENT DOCUMENTS

| | | |
|---|---|---|
| 2,402,703 | 6/1946 | Woodstock . |
| 2,702,299 | 2/1955 | Harris . |
| 3,432,277 | 3/1969 | Roesky ........................................ 23/357 |
| 3,812,221 | 5/1974 | Braden et al. ........................ 260/968 |
| 4,221,583 | 9/1980 | Gaertner et al. . |
| 4,568,432 | 2/1986 | Rogers . |
| 5,128,333 | 7/1992 | Fukuto et al. ...................... 558/167 X |

FOREIGN PATENT DOCUMENTS

| | | | |
|---|---|---|---|
| 300 936 | 9/1992 | Germany ........................ C07F 9/40 |
| 96/15135 | 5/1996 | WIPO . |

OTHER PUBLICATIONS

Abstract–Database WPI, Section Ch, Week 7615, Derwent Publications Ltd., London, GB; Class B04, AN 76–27192X, XP002061354 & JP 51 023 225 A (Nippon Chem. Ind. Co. Ltd.), Feb. 24, 1976.

Blanchard, J. "Préparation d–acides beta–amino–ethyl–phosphoniques" *Tetrahedron*, vol. 32, No. 4, 1976, Oxford GB, pp. 455–459, XP002061374.

Chemical Abstracts, vol. 093, No. 12, Sep. 22, 1980, Columbus, Ohio, US; abstract No. 123612, Zhurba, Y.I. et al. "Increase in the stability of silver complexes in the process of simultaneous developing and fixing" and Zh Nauchn, Pirkl. Fotogr. Kinematogr. (ZNPFAG, 00444561); 80; vol. 25(3); pp. 182–185, Vses. Gos. Nauchno–Issled. Proektn. Inst. Khim.–Fotogr. Prom., Moscow; USSR; XP002061352.

Dyatkina, N. et al. Synthesis and antiviral activity of some fluorinated nucleotide derivativers: Nucleosides Nucleotides (Nunud5, 07328311); 94; col. 13 (1–3); pp. 325–337, Engelhardt Inst. Mol. Biol.; Mowcow; 117984, Russia XP002061348, 1994.

Kashemirov, B.A. "(E)–(Hydroxyimino)(hydroxymethoxyphosphinyl)acetic acid: Synthesis and pH dependent fragmentation," *Tetrahedron Letters*, vol. 36, No. 52, 1995, Oxford GB, pp. 9437–9440; XP002061351.

Albrecht et al., "Reaction of the Two–Component System Trialkyl Phosphite/Carbon Tetrachloride with Nucleophiles 3. Reaction in Presence of Trialkylammonium Salts," *Z. anorg. allg. Chem*.552: 132–146 (1987) and English language translation.

Kashemirov et al., "Troika Acids: Synthesis, Structure, and Fragmentation Pathways of Novel α–(Hydroxyimino)phosphonacetic Acids," *J. Am. Chem. Soc*.117: 7285–7286 (1995).

Shioiri et al., "Reaction of Diethyl Phosphorocyanidate(DEPC) with Carboxylic Acids. A New Synthesis of Carboxylic Esters and Amides," *Tetrahedron*32(18): 2211–2217 (1976).

Tung et al., "A New Method for the Preparation of O,O'–Dialkylphosphoryl Cyanides," *Hua Hsueh Hsueh Pao (Acta Chimica Sinica)*31(3): 199–202 (1965).

*Primary Examiner*—Michael G. Ambrose
*Attorney, Agent, or Firm*—James M. Warner; Arnold, White & Durkee

[57] ABSTRACT

A process for preparing cyanophosphonate derivatives involves contacting a phosphate ester and cyanide in a reaction mixture under conditions sufficient to produce a cyanophosphonate derivative. That cyanophosphonate derivative product can subsequently be hydrogenated to produce an aminomethylphosphonate derivative.

55 Claims, No Drawings

METHOD FOR PREPARING CYANOPHOSPHONATE DERIVATIVES FROM PHOSPHATE ESTERS AND CYANIDE

This application claims the benefit of provisional application Ser. No. 60/034,523, filed Dec. 30, 1996.

BACKGROUND OF THE INVENTION

Phosphorus-containing compounds such as cyanophosphonate derivatives are important precursors for the synthesis of organophosphorus compounds, which have numerous applications, for example, in herbicides, insecticides, fertilizers, flame retardants and plasticizers. Cyanophosphonate derivatives can be further converted to aminomethylphosphonate derivatives, which have been particularly important precursors in the synthesis of N-phosphonomethylglycine, a highly effective commercial herbicide (available under the trade name Roundup™) useful for the control of a large variety of weeds. The syntheses of such organophosphorus compounds have commonly used a halogen derivative of phosphorus as a starting material.

There is a need in the art for alternative processes for preparing cyanophosphonate derivatives and novel cyanophosphonate derivatives to be used in the synthesis of other phosphorus species. There is a further need for such novel processes and compounds that are economical and have an improved environmental impact over conventional processes using halogen-containing starting materials.

SUMMARY OF THE INVENTION

This invention relates to a process for preparing cyanophosphonate derivatives. More particularly, the invention is directed to a process that involves contacting a phosphate ester of the formula:

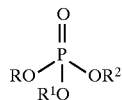

wherein R, $R^1$ and $R^2$ are the same or different and are defined as an aryl group, an arylalkyl group, a vinyl group or a straight or branched alkyl group having from 1 to 20 carbon atoms, and a cyanide in a reaction mixture under sufficient conditions to produce a cyanophosphonate derivative. That cyanophosphonate derivative can be subsequently hydrogenated to produce an aminomethylphosphonate derivative. In a preferred embodiment, the cyanophosphonate derivative and the aminomethylphosphonate derivative are used as precursors for the production of N-phosphonomethylglycine.

The processes according to the invention offer significant advantages in that they provide a novel, economical route to synthesize cyanophosphonate and aminomethylphosphonate derivatives having an improved environmental impact over conventional processes using halogen-containing starting materials.

DESCRIPTION OF ILLUSTRATIVE EMBODIMENTS

The invention is broadly directed to a process that involves contacting a phosphate ester of the formula:

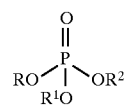

wherein R, $R^1$ and $R^2$ are the same or different and are defined as an aryl group, an arylalkyl group, a vinyl group or a straight or branched alkyl group having from 1 to 20 carbon atoms, and a cyanide in a reaction mixture under sufficient conditions to produce a cyanophosphonate derivative. That cyanophosphonate derivative can be subsequently hydrogenated to produce an aminomethylphosphonate derivative. In a preferred embodiment, the cyanophosphonate and aminomethylphosphonate derivatives produced by the inventive process are precursors for the production of N-phosphonomethylglycine.

The phosphate ester reagent for the cyanophosphonate derivative synthesis according to the invention can be any compound of the formula:

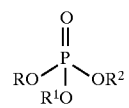

wherein R, $R^1$ and $R^2$ are the same or different and are defined as an aryl group, an arylalkyl group, a vinyl group or a straight or branched alkyl group having from 1 to 20 carbon atoms, and more preferably 1 to 10 carbon atoms. For example, the phosphate ester can be a triarylphosphate, an arylalkylphosphate, a dialkylvinylphosphate, a diarylvinylphosphate or an arylalkylvinylphosphate.

In a preferred embodiment, the aryl group has at least one electron withdrawing substituent, such as a p-nitrophenyl, 2-nitro-4-methylphenyl or 2,6-dichlorophenyl substituent. The aryl group can alternatively have one or more substituents comprising a fluoro, chloro, bromo, fluoromethyl, difluoromethyl, trifluoromethyl, α,α-difluoroethyl, perfluoroethyl, perfluoropropyl, perfluoroalkyl, α,α-difluoroalkyl, an ester, an amide, a ketone, an aldehyde, a sulfone, a sulfoxide, a sulfonate ester, a phosphonate ester, a phosphinate ester, an ammonium ion, a phosphonium ion, a nitro, a pyridine, a pyridine oxide, an amine oxide, a sulfonium ion, a sulfoxonium ion, iodoso or iodosyl carboxylate group. The alkyl group preferably has from 1 to 4 carbon atoms and the arylalkyl group is preferably a benzyl group. The vinyl group preferably has at least one electron withdrawing substituent, such as an ester, a cyano, a nitro, an amido, a phosphonate, a ketone, an aldehyde or a trifluoromethyl group, more preferably an ester substituent.

The cyanide reagent can be hydrogen cyanide or a cyanide salt that is sufficiently reactive with the phosphate ester to produce a cyanophosphonate derivative. For example, the cyanide compound can be an alkali metal cyanide, an alkaline earth metal cyanide, an ammonium cyanide, a tetraalkyl ammonium cyanide, a tetraalkyl phosphonium cyanide, a trialkyl sulfonium cyanide, a cyanide of a cationic form of an organic amine or mixtures thereof. The cyanide compound is preferably hydrogen cyanide, potassium cyanide, sodium cyanide, lithium cyanide, silver cyanide, gold cyanide, copper cyanide, tetrabutylammonium cyanide or mixtures thereof. More preferably, the cyanide reagent is hydrogen cyanide, potassium cyanide, sodium cyanide, lithium cyanide or tetrabutylammonium cyanide. The cyanide is added to the reaction mixture in an amount such that the molar ratio of cyanide ion to phosphate groups added to the reaction mixture is about 1 to about 10, more preferably in the range of about 1 to about 6 or 1 to about 4 and most preferably in the range of about 1.5 to about 3.5.

In a preferred embodiment, the cyanophosphonate derivative synthesis reaction mixture further contains a solvent. The solvent can be any compound suitable for enhancing the solubility of the reactants or providing a medium for the reaction, and is preferably a polar, anhydrous solvent. For example, the solvent is preferably an amide, a nitrile or an ether, for example, N,N-dimethylformamide (DMF), dimethylacetamide, acetonitrile, propionitrile, tetrahydrofuran or methyl t-butyl ether.

The reaction mixture may additionally contain an organic base such as a trialkylamine or an inorganic base such as a carbonate. When the cyanide is hydrogen cyanide, the base is preferably quinuclidine, N-methylpyrrolidine, triethylamine, diglyme, 4-isopropylpyridine, 4-dimethylaminopyridine, tris[2-(2-methoxyethoxy)ethyl]amine, 4-tert-butylpyridine, 4-(5[nonyl)pyridine, trimethylamine, 1,8-bis(dimethylamino)-naphthalene, 4-ethylpyridine, phenanthroline, N,N,N',N'-tetramethylethylenediamine, 1,4,7,10,13-pentamethyl-1,4,7,10,13-pentaazacyclopentadecane, 1,4-diazobicyclo[2.2.2]-octane, 1-butylimidazole, 3-benzylpyridine, 1-5-pentamethylenetetrazole, tris[2(2-methoxyethoxy)ethyl]amine, N,N-dimethylaniline, collidine, N-benzylidine aniline, triphenylphosphine or mixtures thereof. In a further preferred embodiment, when the cyanide is hydrogen cyanide, the base is quinuclidine.

The conditions of the cyanophosphonate derivative synthesis are generally sufficient to promote the formation of the desired cyanophosphonate derivative product in the reaction mixture. The reaction temperature is preferably in the range of about 0° to about 100° C., more preferably in the range of about 20° to about 80° C. and most preferably in the range of about 30° to about 60° C. The reaction is generally conducted with moderate stirring of the reaction mixture. The reaction time can range from about 0.1 to about 72 hours, for example, from about 0.5 to about 15 hours, preferably from about 1 to about 5 hours and most preferably from about 1.5 to about 4 hours.

The cyanophosphonate derivative product, if necessary, is preferably precipitated from the reaction mixture by conventional methods that promote precipitation. For example, the solvent originally added to the reaction mixture can be removed by vacuum pump, and a material such as toluene can be added to the reaction mixture to promote precipitation of the cyanophosphonate derivative product. That composition can then be stirred or settled for a period of time until substantially all of the cyanophosphonate product is precipitated. The resulting precipitate can be further purified, for example, by filtration and/or washing with a solvent such as acetone.

The cyanophosphonate derivative product from the inventive step of contacting the phosphate ester and cyanide can directly or indirectly be a cyanophosphate disalt, a cyanophosphonate monosalt monoester, a cyanophosphonate diester, a cyanophosphonate monosalt monoacid, a cyanophosphonate monoacid monoester or cyanophosphonic acid. Generally, the cyanophosphonate derivative produced is a monosalt monoester or monoacid monoester of cyanophosphonate.

For example, the cyanophosphonate derivative produced by the inventive process can be a salt of benzyl cyanophosphonate, methyl cyanophosphonate, ethyl cyanophosphonate, 5-methyl-2-nitrophenylcyanophosphonate, p-nitrophenylcyanophosphonate, 2,6-dichlorophenylcyanophosphonate, 2-nitro-4-methylphenylcyanophosphonate or 4-nitrophenylcyanophosphonate. The salt is a preferably a potassium, sodium, lithium, trialkylammonium, quinuclidinium, tetraalkylammonium or tetrabutyl ammonium salt. The benzyl esters of cyanophosphonate can be further hydrogenolyzed to produce cyanophosphonate mono- or disalts. The cyanophosphonate derivative product is preferably produced in at least 20% yield with respect to the phosphate reagent, for example, at a 20 to 65% yield, wherein the yield is defined as the [cyanophosphonate derivative product]/[phosphate ester reagent].

The cyanophosphonate derivative produced in the above synthesis can be used as a precursor for producing other organophosphorus species. In a preferred embodiment, the cyanophosphonate derivative product can be hydrogenated to produce an aminomethylphosphonate derivative. The hydrogenation can take place by contacting the cyanophosphonate derivative with hydrogen in the presence of a suitable catalyst under sufficient conditions to produce an aminomethylphosphonate derivative. The cyanophosphonate derivative can be provided alone or in a mixture of compounds, including a product mixture or portion of a product mixture from the reaction of a phosphate ester and cyanide.

Preferably, the hydrogenation further involves the presence of a solvent. The solvent can be any material that enhances the solubility of reactants or promotes the formation of the desired products. In a preferred embodiment, the solvent is water, acetic acid, an alcohol, dimethylacetamide, an anhydride, e.g., acetic anhydride, an amide, sulfolane or mixtures thereof.

Hydrogen pressure can be maintained at a level suitable for the formation of an aminomethylphosphonate derivative, and consistent with safety limitations of the experimental system. In a preferred embodiment, the hydrogen pressure is between about 0.25 and 5000 psi, more preferably between about 0.5 and about 3000 psi and most preferably between about 1 and about 1000 psi, for example, between about 25 and about 300 psi.

In a preferred embodiment, the catalyst is a transition metal catalyst. For example, the hydrogenation step can use a catalyst of a cobalt-containing compound, a nickel-containing compound, a platinum-containing compound, a palladium-containing compound or a rhodium-containing compound. More preferably, the catalyst is Raney cobalt, Raney nickel, platinum promoted Raney nickel such as platinum tetrachloride ($PtCl_4$) promoted Raney nickel, platinum on carbon, palladium on carbon or rhodium on carbon. The catalyst can be used at a stoichiometric amount or catalytic amount with respect to the cyanophosphonate derivative. The stoichiometric amount is preferably between about 1 molar equivalent and 5 molar equivalents with respect to the cyanophosphonate derivative, and more preferably between about I molar equivalent and 2 molar equivalents with respect to the cyanophosphonate derivative. The catalytic amount is preferably between about 0.1 molar percent and 100 molar percent with respect to the cyanophosphonate derivative, and more preferably between about 0.5 molar percent and 50 molar percent with respect to the cyanophosphonate derivative.

In the event that a catalyst of platinum on carbon, palladium on carbon or rhodium on carbon is used, the hydrogenation reaction mixture preferably further contains an acid in an amount sufficient to promote formation of the desired product. The acid can be an inorganic acid or an organic acid. The inorganic acid is preferably hydrochloric acid, sulfuric acid, phosphoric acid, nitric acid or hydrocyanic acid and more preferably, hydrochloric acid. The organic acid is preferably acetic acid, trifluoroacetic acid, trifluoromethanesulfonic acid, or p-toluenesulfonic acid. The acid can be present at a concentration between about 0.1 and 5 molar equivalents with respect to the cyanophosphonate derivative, more preferably at a concentration between about 0.5 and 2.5 molar equivalents with respect to the cyanophosphonate derivative, and most preferably at a concentration of about 1 molar equivalent or about 2 molar equivalents with respect to the cyanophosphonate derivative, depending on the degree of protonation.

In a preferred embodiment, the reaction product mixture from the hydrogenation step is heated under sufficient conditions to further promote the formation of the aminomethylphosphonate derivative. For example, a product mixture that has been partially or substantially hydrogenated can be heated to a temperature in the range of about 135° C. to about 200° C., and more preferably to a range of about 135° C. to about 160° C. This heating step may be conducted for any amount of time that further promotes the aminomethylphosphonate derivative formation, preferably about 1 to about 12 hours. The heating time for optimum aminomethylphosphonate derivative formation can depend on the pH and the nature of the cations in the reaction mixture.

The products of the hydrogenation step can be isolated from the reaction mixture by conventional methods or can be used for some purposes without isolation from the reaction product mixture. Further details regarding cyanophosphonate derivative hydrogenation are provided in co-pending U.S. application Ser. No. 08/996,948, entitled "Method for Preparing Aminomethylphosphonate Derivatives Via Hydrogenation of Cyanophosphonate Derivatives," by Patrick J. Lennon, filed Dec. 23, 1997, which is incorporated herein by reference.

The aminomethylphosphonate derivative product of the inventive process can be used as a precursor for producing other organophosphorus species. In a preferred embodiment, aminomethylphosphonic acid is used for producing N-phosphonomethylglycine. Methods for producing N-phosphonomethylglycine from aminomethylphosphonic acid are disclosed, for example, in U.S. Pat. No. 4,221,583 (Monsanto Co.), which is incorporated herein by reference.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The following Examples 1–7 were conducted by mixing one equivalent of phosphate with one, two or three equivalents of lithium cyanide in DMF under magnetic stirring. The reaction mixture was heated then to the desired temperature. The formation of the cyanophosphonic derivatives was detected by $^{31}$p NMR and mass spectral analysis.

Example 1

Lithium cyanide (2.5 ml of a 0.5M solution in DMF, 1.25 mmol) was added to diethyl 4-nitrophenyl phosphate (0.138 g, 0.5 mmol). The reaction mixture was heated to 50° C. for 16 hours. The formation of 9% ethyl cyanophosphonate was indicated by the $^{31}$P NMR (DMF) showing a resonance at δ (ppm) –23.0 (t, $^3J_{PH}$=8.4 Hz) which contained 9% of the $^{31}$P NMR signals. Mass spectral analysis (FAB-, TGL) detected the peak at m/z 134, corresponding to the anion species [NCP(O)(OC$_2$H$_5$)O—].

Example 2

Lithium cyanide (1 ml of a 0.5M solution in DMF, 0.5 mmol) solution in DMF was added to 0.138 g (0.5 inmol) of diethyl 4-nitrophenyl phosphate. The reaction mixture was heated to 40° C. for 72 hours and showed the formation of 7% ethyl cyanophosphonate: $^{31}$p NMR (DMF) δ (ppm) –23.0 (t, $^3J_{PH}$=8.4 Hz).

Example 3

Lithium cyanide (1 ml of a 0.5M solution in DMF, 0.5 mmol) was added to 0.138 g (0.5 mmol) of diethyl 4-nitrophenyl phosphate. The reaction mixture was heated at 40° C. for 2 hours and showed the formation of about 7% ethylcyanophosphonate: $^{31}$P NMR (DMF) δ (ppm) –23.0 (t, $^3J_{PH}$=8.4 Hz). Additional heating for 3 hours did not change the spectrum. A second portion of lithium cyanide (1 ml of a 0.5M solution in DMF, 0.5 mmol) was then added, and the reaction mixture was heated at 40° C. for 5 hours giving 20% ethylcyanophosphonate product according to $^{31}$p NMR.

Example 4

Lithium cyanide (1 ml of a 0.5M solution in DMF, 0.5 mmol) was added to tris(5-methyl-2-nitrophenyl)phosphate (0.252 g, 0.5 mmol) dissolved in 1 ml DMF. The reaction mixture was heated at 80° C. for 3 hours and showed the formation of 15% 5-methyl-2-nitrophenylcyanophosphonate acid derivative, 66% lithium bis(5-methyl-2-nitrophenyl)phosphate, and 18% starting material: 31P NMR (DMF) δ (ppm) –29.5, –15.5, and –21, respectively. Mass spectral analysis (FAB-, TGL) detected peaks at m/z 241, 367, and 152 corresponding to the anionic species (NCP(O)(OC$_6$H$_3$CH$_3$NO$_2$)O—], [(O)P(OC$_6$H$_3$CH$_3$NO$_2$)$_2$O—] and [2-NO$_2$-4-CH$_3$C$_6$H$_3$O—-], respectively . Additional heating for 30 minutes did not change the spectrum. A second portion of lithium cyanide (1 ml of a 0.5M LiCN solution in DMF, 0.5 mmol) was then added, and the reaction mixture was heated at 80° C. for 30 minutes giving the following products in the ratio 1:5, (NCP(O)(OC$_6$H$_3$CH$_3$NO$_2$)OLi:(O)P(OC$_6$H$_3$CH$_3$NO$_2$)$_2$OLi).

Example 5

Lithium cyanide (2.0 ml of a 0.5M solution in DMF, 1.0 mmol) was added to 2-carbomethoxy-1-methylvinyldimethyl phosphate (0.11 g, 0.5 mmol). The reaction mixture was heated at 80° C. for 16 hours, and the resulting product showed by $^{31}$P NMR and mass spectral analysis the formation of 37% methylcyanophosphonate, 58% bis(2-carbomethoxy-1-methylvinylmethyl phosphate, and a trace amount of phosphates: $^{31}$p NMR (DMF) δ (ppm) –30 (q, $^3J_{PH}$=12.2 Hz), –16.0 (quartet, $^3J_{PH}$=10.7 Hz), and 0 (septet), respectively. Mass spectral analysis (FAB-, TGL) showed peaks at m/z 120, 209, and 125 corresponding to the anionic species [NCP(O)(OCH$_3$)O—], [(O)P(OCH$_3$)(O(CH$_3$)C═C(H)COOCH$_3$)O—], and [(O)P(OCH$_3$)$_2$O—], respectively.

Example 6

Lithium cyanide (2.0 ml of a 0.5M solution in DMF, 1.0 mmol) was added to tris(p-nitrophenyl)phosphate (0.23 g, 0.5 mmol). The reaction mixture was heated at 80° C. for 30 minutes, and the resulting product showed the formation of 24% lithium p-nitrophenylcyanophosphonate, 70% bis(p-nitrophenyl)phosphate, and a trace amount of phosphates: $^{31}$P NMR (DMF) δ (ppm) −30, −16.0, and −1 to −5 range, respectively. Mass spectral analysis (FAB-, TGL) showed peaks at m/z 227 and 339 corresponding to [NCP(O)(OC$_6$H$_4$NO$_2$)O—] and [(O)P(OC$_6$H$_4$NO$_2$)$_2$O—], respectively.

Example 7

Lithium cyanide (2.0 ml of a 0.5M solution in DMF, 1.0 mmol) was added to tris(2,6-dichlorophenyl)phosphate (0.267 g, 0.5 mmol). The reaction mixture was heated at 80° C. for 16 hours, and the resulting product showed the formation of 28% lithium 2,6-dichlorophenylcyanophosphonate, 13% lithium bis(2,6-dichlorophenyl)phosphate, 9% other phosphates, and 50% of the starting material. A second portion of lithium cyanide (1 ml of a 0.5M solution in DMF, 0.5 mmol) was added, and the reaction mixture was heated at 80° C. for 24 hours, and the resulting product according to $^{31}$P NMR contained 61% of lithium 2,6-dichlorophenylcyanophosphonate, 32.5% bis (2,6-dichloro-phenyl)phosphate, and 6.5% other phosphates: $^{31}$P NMR (DMF) δ (ppm) −31.0, −15.2, 1.5 to −5 respectively. Mass spectral analysis (FAB-, NBA) showed peaks at m/z 250, 385, and 161 corresponding to the anionic species [NCP(O)(OC$_6$H$_3$Cl$_2$)O−], [(O)P(OC$_6$H$_3$Cl$_2$)$_2$O—] and [2,6-Cl$_2$C$_6$H$_3$O—], respectively.

Example 8

Liquid hydrocyanic acid (0.5 ml, 12.7 mmol, distilled from 1.7 g H$_2$SO$_4$ in 0.7 ml H$_2$O and 0.035 g FeSO$_4$ a mixture of K$^2$CN (1.28 g) and K$^{13}$CN (1.0 g) in 4 ml H$_2$O) added to mixture of tris(2,6-dichlorophenyl)phosphate (2.29 g, 4.3 mmol) and quinuclidine (1.44 g, 12.27 mmol) in 15 ml DMF cooled in an ice bath. The reaction mixture was heated with stirring for 8 hours at 80° C. and was kept for 16 hours at room temperature. The resulting product showed the formation of 38% (2,6-Cl$_2$ArO)(O)(CN)PO: $^{31}$P NMR (DMF) −29.3 ppm (t, $^1$J$_{PC}$=180.1 Hz), $^{13}$C NMR -119.8 ppm (d, $^1$J$_{CP}$=180.3 Hz); 4% of another P—CN containing compound $^{31}$P NMR (DMF) −11.5 ppm (t, $^1$J$_{PC}$=119.0 Hz), $^{13}$C NMR 120.6 ppm (d, $^1$J$_{CP}$=118.2 Hz); 20% (2,6-Cl$_2$ArO)$_2$(O—)PO, $^{31}$P NMR (DMF) −12.5 ppm (s): 27% starting material: $^{31}$P NMR (DMF) −22.2 ppm; there were a few weak signals in $^{31}$p NMR spectrum at −9 ppm, −0.5 ppm, and 3 ppm, corresponding to compounds without P—CN bonds.

Example 9

12 mL of 0.5M LiCN (6 mmol) solution in DMF was added to the mixture of 0.666 g (1 mmol) of K$^{13}$CN and 1.06 g (2 mmol) of tris(2,6-dichlorophenyl)phosphate. The reaction mixture was kept at 30° C. for 5 days, and the resulting product showed the formation of 88.4% 2,6-dichlorophenylcyanophosphonate salt and 11.6% lithium bis(2,6-dichlorophenyl)phosphate derivative: $^{31}$p NMR (DMF) δ (ppm) −29.8 (s), $^{13}$C sideband doublet J$_{PC}$=184.6 Hz, and −14.2, respectively.

Example 10

0.6 mL of 0.5M LiCN (0.3 mmol) solution in DMF was added to 0.052 g (0.1 mmol) of tris(2,6-dichlorophenyl) phosphate. The reaction mixture was kept at room temperature for 30 minutes, and the resulting product showed the formation of 86% lithium 2,6-dichlorophenylcyanophosphonate and 14% lithium bis(2,6-dichlorophenyl)phosphate: $^{31}$p NMR (DMF) δ (ppm) −30.0 and −14.2, respectively.

Example 11
General Procedure for Low Pressure Hydrogenations

Dipotassium cyanophosphonate (0.133 g, 1.0 mmol) was added to Raney nickel (0.118 g, as a 50% slurry in water, W2 form) in a Fisher Porter bottle containing a stir bar. Water (5 ml) was added, and platinum tetrachloride (0.105 g, 0.31 mmol) was added. The pressure bottle was immediately connected to a hydrogen manifold, and three purges with hydrogen at 75 psi were done, and the bottle was pressurized to 75 psi. The reaction mixture was vigorously stirred for 25.5 hours at room temperature. The pressure was then released and the reaction mixture was filtered. HPLC Analysis determined a 63% yield of aminomethylphosphonic acid,

Example 12
General Procedure for Hydrogenation in Autoclave

In a 300 ml Autoclave Engineers autoclave, Na$_2$O$_3$PCN (H2O)$_{0.49}$ (0.80 g, 5.0 mmol) was added, followed by 10% Pt/C (0.15 g), water (100 ml), and then HCl•dioxane (2.5 ml, 4N, 10.0 ml). The autoclave was sealed, pressured once with nitrogen above 500 psi, vented, and pressured with hydrogen to 1001 psi. Stirring at about 1500 rpm was started. Within about 10 minutes, the internal pressure was about 996 psi, and the autoclave internal temperature was about 26° C. After stirring overnight, the hydrogen was vented, the autoclave was repressurized with nitrogen and vented, and then the reactor was opened and the reaction mixture removed. The reaction mixture was filtered, and the resulting solution analyzed by HPLC. The yield by HPLC of aminomethylphosphonic acid was 85%, and by NMR 87%.

While the compositions and methods of this invention have been described in terms of preferred embodiments, it will be apparent to those of skill in the art that variations can be applied to the process described herein without departing from the concept, spirit and scope of the invention. All such similar substitutes and modifications apparent to those skilled in the art are deemed to be within the spirit, scope and concept of the invention.

What is claimed is:

1. A process for preparing a cyanophosphonate derivative comprising:

contacting a phosphate ester of the formula:

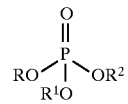

wherein R, R$^1$ and R$^2$ are the same or different and are defined as an aryl group, an arylalkyl group, a vinyl group or a straight or branched alkyl group having from 1 to 20 carbon atoms, and a cyanide in a reaction mixture under sufficient conditions to produce a cyanophosphonate derivative.

2. The process of claim 1, wherein the aryl, arylalkyl, vinyl or alkyl groups have from 1 to 10 carbon atoms.

3. The process of claim 1, wherein the aryl group has at least one electron withdrawing substituent.

4. The process of claim 3, wherein the aryl group is a p-nitrophenyl, 2-nitro-4-methylphenyl or 2,6-dichlorophenyl substituent.

5. The process of claim 2, wherein the alkyl group has from 1 to 4 carbon atoms.

6. The process of claim 2, wherein the arylalkyl group is a benzyl group.

7. The process of claim 1, wherein the vinyl group has at least one electron withdrawing substituent.

8. The process of claim 7, wherein the electron withdrawing substituent is an ester, a cyano, a nitro, an amido, a phosphonate, a ketone, an aldehyde or a trifluoromethyl substituent.

9. The process of claim 8, wherein the electron withdrawing substituent is an ester substituent.

10. The process of claim 1, wherein the phosphate ester is a triarylphosphate.

11. The process of claim 1, wherein the phosphate ester is an arylalkylphosphate.

12. The process of claim 1, wherein the phosphate ester is a dialkylvinylphosphate.

13. The process of claim 1, wherein the phosphate ester is a diarylvinylphosphate.

14. The process of claim 1, wherein the phosphate ester is an arylalkylvinylphosphate.

15. The process of claim 1, wherein the phosphate ester is diethyl 4-nitrophenyl phosphate, tris(5-methyl-2-nitrophenyl)phosphate, 2-carbomethoxy-1-methylvinyldimethyl phosphate, tris-(p-nitrophenyl) phosphate or tris(2,6-dichlorophenyl)phosphate.

16. The process of claim 1, wherein the cyanide is soluble in the reaction mixture.

17. The process of claim 1, wherein the cyanide is hydrogen cyanide, an alkali metal cyanide, an alkaline earth metal cyanide, an ammonium cyanide, a tetraalkyl ammonium cyanide, a tetraalkyl phosphonium cyanide, a trialkyl sulfonium cyanide, a cyanide of a cationic form of an organic amine or mixtures thereof.

18. The process of claim 17, wherein the cyanide is hydrogen cyanide, potassium cyanide, sodium cyanide, lithium cyanide, silver cyanide, gold cyanide, copper cyanide, tetrabutyl-ammonium cyanide or mixtures thereof.

19. The process of claim 18, wherein the cyanide is hydrogen cyanide, potassium cyanide, sodium cyanide, lithium cyanide or tetrabutylammonium cyanide.

20. The process of claim 1, wherein the molar ratio of cyanide ion to phosphate groups added to the reaction mixture is in the range of about 1 to about 10.

21. The process of claim 20, wherein the molar ratio of cyanide ion to phosphate groups added to the reaction mixture is in the range of about 1 to about 6.

22. The process of claim 21, wherein the molar ratio of cyanide ion to phosphate groups added to the reaction mixture is in the range of about 1.5 to about 3.5.

23. The process of claim 1, wherein the temperature of the reaction mixture during the contacting is in the range of about 0° to about 100° C.

24. The process of claim 23, wherein the temperature of the reaction mixture during the contacting step is in the range of about 20° to about 80° C.

25. The process of claim 24, wherein the temperature of the reaction mixture during the contacting step is in the range of about 30° to about 60° C.

26. The process of claim 1, wherein the reaction mixture further contains a solvent.

27. The process of claim 26, wherein the solvent is a polar solvent.

28. The process of claim 26, wherein the solvent is an anhydrous solvent.

29. The process of claim 26, wherein the solvent comprises an amide, a nitrile or an ether.

30. The process of claim 29, wherein the solvent comprises DMF or dimethylacetamide.

31. The process of claim 29, wherein the solvent comprises acetonitrile or propionitrile.

32. The process of claim 29, wherein the solvent comprises tetrahydrofuran or methyl t-butylether.

33. The process of claim 1, wherein the cyanophosphonate derivative is a cyanophosphonate monoester monosalt.

34. The process of claim 1, wherein the cyanophosphonate derivative is a salt of benzyl cyanophosphonate, methyl cyanophosphonate, ethyl cyanophosphonate, 5-methyl-2-nitrophenylcyanophosphonate, 2-nitro-4-methylphenylcyanophosphonate, 4-nitrophenylcyanophosphonate, p-nitrophenylcyanophosphonate or 2,6-dichlorophenylcyanophosphonate.

35. The process of claim 34, wherein the salt is a potassium, sodium or lithium salt.

36. The process of claim 34, wherein the salt is a trialkylammonium, a quinuclidinium, a tetraalkylammonium or a tetrabutylammonium salt.

37. The process of claim 1, wherein the cyanophosphonate derivative is a monoester monoacid of cyanophosphonate or a monosalt monoester of cyanophosphonate.

38. The process of claim 1, wherein the cyanophosphonate derivative is methyl cyanophosphonate or ethyl cyanophosphonate.

39. A process for preparing an aminomethylphosphonate derivative comprising:

contacting a phosphate ester of the formula:

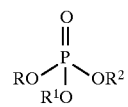

wherein R, $R^1$ and $R^2$ are the same or different and are defined as an aryl group, an arylalkyl group, a vinyl group or a straight or branched alkyl group having from 1 to 20 carbon atoms, and a cyanide in a reaction mixture under sufficient conditions to produce a cyanophosphonate derivative; and hydrogenating the cyanophosphonate derivative in the presence of a suitable catalyst under sufficient conditions to produce an aminomethylphosphonate derivative.

40. The process of claim 39, wherein the cyanophosphonate derivative is a salt of benzyl cyanophosphonate, methyl cyanophosphonate, ethyl cyanophosphonate, 5-methyl-2-nitrophenylcyanophosphonate, 2-nitro-4-methylphenylcyanophosphonate, 4-nitrophenylcyanophosphonate, p-nitrophenyl-cyanophosphonate or 2,6-dichlorophenylcyanophosphonate.

41. The process of claim 40, wherein the salt is a potassium, sodium or lithium salt.

42. The process of claim 41, wherein the salt is a trialkylammonium, a quinuclidinium, a tetraalkylammonium or a tetrabutylammonium salt.

43. The process of claim 39, wherein the cyanophosphonate derivative is methyl cyanophosphonate or ethyl cyanophosphonate.

44. The process of claim 39, wherein the catalyst is a cobalt-containing compound, a nickel-containing compound, a rhodium-containing compound, a platinum-containing compound or a palladium-containing compound.

45. The process of claim 44, wherein the catalyst is Raney cobalt, Raney nickel, platinum tetrachloride ($PtCl_4$) promoted Raney nickel, platinum on carbon, palladium on carbon or rhodium on carbon.

46. The process of claim 45, wherein the catalyst is a Raney nickel catalyst.

47. The process of claim 45, wherein the catalyst is a platinum promoted Raney nickel catalyst.

48. The process of claim 47, wherein the catalyst is a platinum tetrachloride ($PtCl_4$) promoted Raney nickel catalyst.

49. The process of claim 43, wherein the catalyst is rhodium on carbon, platinum on carbon or palladium on carbon.

50. The method of claim 49, wherein the hydrogenation reaction mixture further contains an acid.

51. The method of claim 50, wherein the acid is an inorganic acid.

52. The method of claim 51, wherein the inorganic acid is hydrochloric acid, sulfuric acid, phosphoric acid or nitric acid.

53. The method of claim 52, wherein the inorganic acid is hydrochloric acid.

54. The method of claim 50, wherein the acid is an organic acid.

55. The method of claim 54, wherein the organic acid is acetic acid, trifluoroacetic acid, trifluoromethanesulfonic acid or p-toluenesulfonic acid.

* * * * *